United States Patent
Stewart et al.

(10) Patent No.: US 6,769,287 B2
(45) Date of Patent: Aug. 3, 2004

(54) APPARATUS FOR TESTING STRUCTURAL COMPONENT SAMPLES BY IMPACTING WITH ICE BALLS

(75) Inventors: John David Stewart, Southlake, TX (US); Scott James Morrison, Southlake, TX (US); Johnie Pollard Spruiell, Southlake, TX (US); Matthew John Sitzmann, Dallas, TX (US); Patrick Thomas Price, Flower Mound, TX (US); Steven Richard Smith, Irving, TX (US)

(73) Assignee: Haag Engineering Co., Carrollton, TX (US)

( * ) Notice: Subject to any disclaimer, the term of this patent is extended or adjusted under 35 U.S.C. 154(b) by 7 days.

(21) Appl. No.: 10/321,294

(22) Filed: Dec. 17, 2002

(65) Prior Publication Data

US 2004/0112353 A1 Jun. 17, 2004

(51) Int. Cl.[7] .............................. G01P 15/00; F41B 7/00
(52) U.S. Cl. ..................................... 73/12.01; 124/20.1
(58) Field of Search .............................. 73/12.01, 12.04, 73/12.05, 12.07, 12.09, 12.11; 124/20.1, 20.2

(56) References Cited

U.S. PATENT DOCUMENTS

| | | | |
|---|---|---|---|
| 3,130,575 A | | 4/1964 | Rogers |
| 3,343,400 A | | 9/1967 | Rogers et al. |
| 3,380,290 A | | 4/1968 | Michelson |
| 3,426,578 A | | 2/1969 | Bergs et al. |
| 3,563,132 A | * | 2/1971 | Cashen et al. ............. 89/33.14 |
| 3,605,482 A | | 9/1971 | Humes |
| 3,868,113 A | | 2/1975 | Glass et al. |
| 3,879,982 A | | 4/1975 | Schmidt |
| 3,896,657 A | | 7/1975 | Brandt et al. |
| 4,034,603 A | | 7/1977 | Leeb et al. |
| 4,131,012 A | | 12/1978 | Courtiol |
| 4,168,620 A | | 9/1979 | Schrader |
| 4,201,078 A | | 5/1980 | Morinaga |
| 4,236,402 A | | 12/1980 | McGuire |
| 4,313,337 A | | 2/1982 | Myint |
| 4,349,200 A | | 9/1982 | Wakefield |
| 4,405,243 A | | 9/1983 | Kuraoka et al. |
| 4,418,563 A | | 12/1983 | Kalthoff et al. |
| 4,433,570 A | | 2/1984 | Brown et al. |
| 4,435,976 A | | 3/1984 | Edward, Jr. |
| 4,437,333 A | | 3/1984 | Hands |
| 4,531,400 A | | 7/1985 | Nevel |
| 4,574,238 A | * | 3/1986 | Weinlich ..................... 324/178 |
| 4,688,539 A | * | 8/1987 | Lawrence .................... 124/27 |
| 4,696,182 A | | 9/1987 | Meir |
| 4,776,202 A | | 10/1988 | Brar et al. |
| 4,860,572 A | | 8/1989 | Brar et al. |
| 5,036,696 A | | 8/1991 | Ahrens et al. |
| 5,123,643 A | | 6/1992 | Heilhecker et al. |

(List continued on next page.)

Primary Examiner—Edward Lefkowitz
Assistant Examiner—T. Miller
(74) Attorney, Agent, or Firm—Dennis T. Griggs (57) ABSTRACT

An ice ball launcher simulates the impact of a storm-generated hailstone falling onto a test specimen or structural component exhibit such as a roofing shingle, skylight, automobile panel, aircraft fuselage panel, aircraft wing panel and the like. The launcher includes a tripod base, a rail, a sled, an ice ball holder cup, a manually operable trigger latch assembly, an elastic band and a laser beam aiming device. The ice ball launcher consistently and repeatably projects ice balls at a predetermined velocity and impact energy onto the component sample. The velocity of each ice ball is measured as it transits from the ice ball launcher to the installation mockup, verifying that the ice ball velocity is within a predetermined velocity tolerance range. The measured velocity and known mass of the ice ball are used to calculate the kinetic impact energy on the component sample material, and to determine whether the calculated impact energy is within a predetermined impact energy tolerance range.

30 Claims, 8 Drawing Sheets

U.S. PATENT DOCUMENTS

| | | | |
|---|---|---|---|
| 5,129,852 A | * | 7/1992 | Crisci et al. .................. 446/60 |
| 5,184,499 A | | 2/1993 | Oppliger et al. |
| 5,242,830 A | | 9/1993 | Argy et al. |
| 5,297,418 A | | 3/1994 | Champaigne |
| 5,412,995 A | | 5/1995 | Smith et al. |
| 5,540,078 A | | 7/1996 | Ambur et al. |
| 5,567,867 A | | 10/1996 | Nazar |
| 5,579,750 A | | 12/1996 | Lease |
| 6,050,127 A | | 4/2000 | Rao et al. |
| 6,219,930 B1 | | 4/2001 | Reid |
| 6,595,160 B1 | * | 7/2003 | Williamson ................ 124/20.1 |
| 2003/0071077 A1 | * | 4/2003 | Panzarella .................. 222/386 |

* cited by examiner

*Fig. 12*

APPARATUS FOR TESTING STRUCTURAL COMPONENT SAMPLES BY IMPACTING WITH ICE BALLS

BACKGROUND OF THE INVENTION

This invention relates generally to impact testing apparatus, and in particular to launch apparatus for consistently and precisely projecting ice balls for testing structural component materials in connection with product grading and performance studies, new product design evaluation, as well as structural failure and property damage analysis, for example in simulating hail damage to roof shingles, skylights, vehicle windshields, automobile roof panels, aircraft fuselage panels, aircraft wing panels and the like.

Hail is showery precipitation in the form of irregular pellets or balls of ice typically more than about ⅓ inch in diameter. Hail usually free-falls from a cumulonimbus cloud. Sometimes severe thunderstorms or tornadic storms bring about hail storms. Hail is a major cause of damage to structures such as roof shingles, skylights, vehicle windshields, automobile roof panels and aircraft fuselage panels, leading to many insurance claims. Although conventional impact test procedures and equipment have been devised for assessing the structural integrity and strength of various structural component materials, such equipment for simulating the effect of hail impact has not previously been available. The ability of a material to resist hail damage is of considerable interest to structural engineers and the insurance underwriting industry.

There is, therefore, a need for impact test equipment that can repeatedly and precisely project ice balls at predetermined, consistent impact energy levels in connection with a testing protocol that simulates the impact of hail on various materials to determine relative ability or strength of a building material or structural component to withstand hail damage. Such equipment is needed, for example, for testing structural materials in connection with product quality grading and performance studies, new product design and development evaluations, as well as structural failure and property damage analysis, for example in simulating hail damage to roof shingles.

BRIEF SUMMARY OF THE INVENTION

In accordance with one aspect of the present invention, an ice ball launcher is provided. The ice ball launcher includes a base member, a rail, a sled, an ice ball holder, a trigger latch assembly, one or more elastic bands and an aiming device. The rail is adjustably attached to the base member, and the rail has a channel portion thereon. The sled is slidably coupled with the channel portion on the rail. The ice ball holder is removably attached to the sled. The ice ball holder has an interior configuration adapted to bias against and releasably retain an ice ball therein. One or more elastic bands extend to and engage with the sled. The launcher is configured such that the elastic band is in a stretched condition under predetermined tension pulling on the sled when the sled is in a cocked position and the trigger latch assembly is engaged. The aiming device is attached to the base member in alignment with the rail, assuring precision placement of the ice ball impact onto a target area of interest. A protective shield is attached to the base member and extends generally perpendicular to the rail.

In accordance with another aspect of the present invention, an ice ball launcher is provided in which the ice ball holder includes a cup member that has a groove formed there through that extends partially about the cup member in a circumferential direction. A reed member is attached to an interior surface of the cup member at one end of the reed member such that the reed member extends across at least a portion of the groove. The elastic band is located about the cup member within the groove. The elastic band has a relaxed diameter less than the outer diameter of the cup member where the groove is located such that the elastic band extends into the cup member and biases against the reed member.

The aiming device is attached to the base member in alignment with the longitudinal axis of the rail. In the preferred embodiment the aiming device includes a low power laser that emits a visible laser beam that projects a small red dot onto the target surface. Column posts are mounted on either side of the rail for engaging the band and arresting forward movement of the sled at a predetermined travel limit stop point. The column posts serve as stops for engaging a central portion of the elastic band to limit a range of forward motion of the sled. The ice ball is only lightly retained within the cup and the retaining force applied by the holder is easily overcome by the forward momentum and kinetic energy of the ice ball as movement of the sled is arrested at the stop point.

According to one aspect of the invention, a velocity measuring apparatus is provided to measure the velocity of an ice ball as it is projected from the ice ball launcher. The ice ball velocity measurement is taken in order to calculate the impact energy and thus assure that the impact energy on target is within a desired tolerance range for uniform testing purposes. The velocity measuring apparatus includes a first light source, a first light sensor, a second light source, a second light sensor, and an electrical timing circuit. The first light sensor is positioned to receive light from the first light source. The second light sensor is positioned to receive light from the second light source. The second light sensor is located at a fixed distance away from the first light sensor. The electrical circuit is adapted to: detect a change in output from the first light sensor; detect a change in output from the second light sensor; measure a time between the detected change in output from the first light sensor and the detected change in output from the second light sensor, and calculate the velocity of an ice ball first passing between the first light source and the first light sensor and then passing between the second light source and the second light sensor.

In accordance with yet another aspect of the present invention, a method of simulating hail stone impact is provided for testing structural component samples, for example roof shingles. The method includes the following steps, the order of which may vary. First, an ice ball of a predetermined size is molded. Next, an installation mock-up (e.g., a roof section) having component samples (e.g., roofing shingles) installed thereon is set up. Then, the ice ball launcher is set up at a predetermined distance from the installation mock-up and aimed generally at a predetermined projection angle toward the mockup. The sled is then retracted to the latched position in which the elastic band is stretched to a predetermined tension level, and an ice ball is loaded into the cup. The launcher is then aimed precisely with the aid of a laser beam onto a desired target area. The trigger is manually actuated, thus releasing the sled, and the ice ball is projected from the cup at a predetermined velocity within a predetermined velocity range onto a specific location on the component sample within an aiming point area tolerance.

The method may further include the steps of measuring the velocity of the ice ball as it projects from the ice ball launcher to the installation mockup, verifying that the ice ball velocity is within the predetermined velocity tolerance range, calculating an impact energy of the ice ball impacting the component sample material, and determining whether the calculated impact energy is within a predetermined impact energy tolerance range.

BRIEF DESCRIPTION OF THE DRAWING

The accompanying drawing figures are incorporated into and form a part of this specification to illustrate preferred embodiments of the present invention. Various advantages and features of the invention will be understood from the following detailed description taken with reference to the attached drawing figures in which.

DETAILED DESCRIPTION OF PREFERRED EMBODIMENT

Preferred embodiments of the invention will now be described with reference to various examples of how the invention can best be made and used. Like reference numerals are used throughout the description and several views of the preferred embodiment to indicate like or corresponding parts.

In general, the present invention provides a method and apparatus for simulating the impact of a storm-generated free-fall hailstone falling from the sky onto a test specimen or exhibit such as a roof shingle, skylight, automobile panel, aircraft panel or the like. The present invention provides an ice ball launcher that can consistently and repeatably project an ice ball at a predetermined velocity and impact energy onto the test specimen or exhibit. The ice ball launcher of the present invention can be reliably aimed at a precise location or target area on a test specimen to provide accurate and controllable impact locations during testing.

Figure 1:
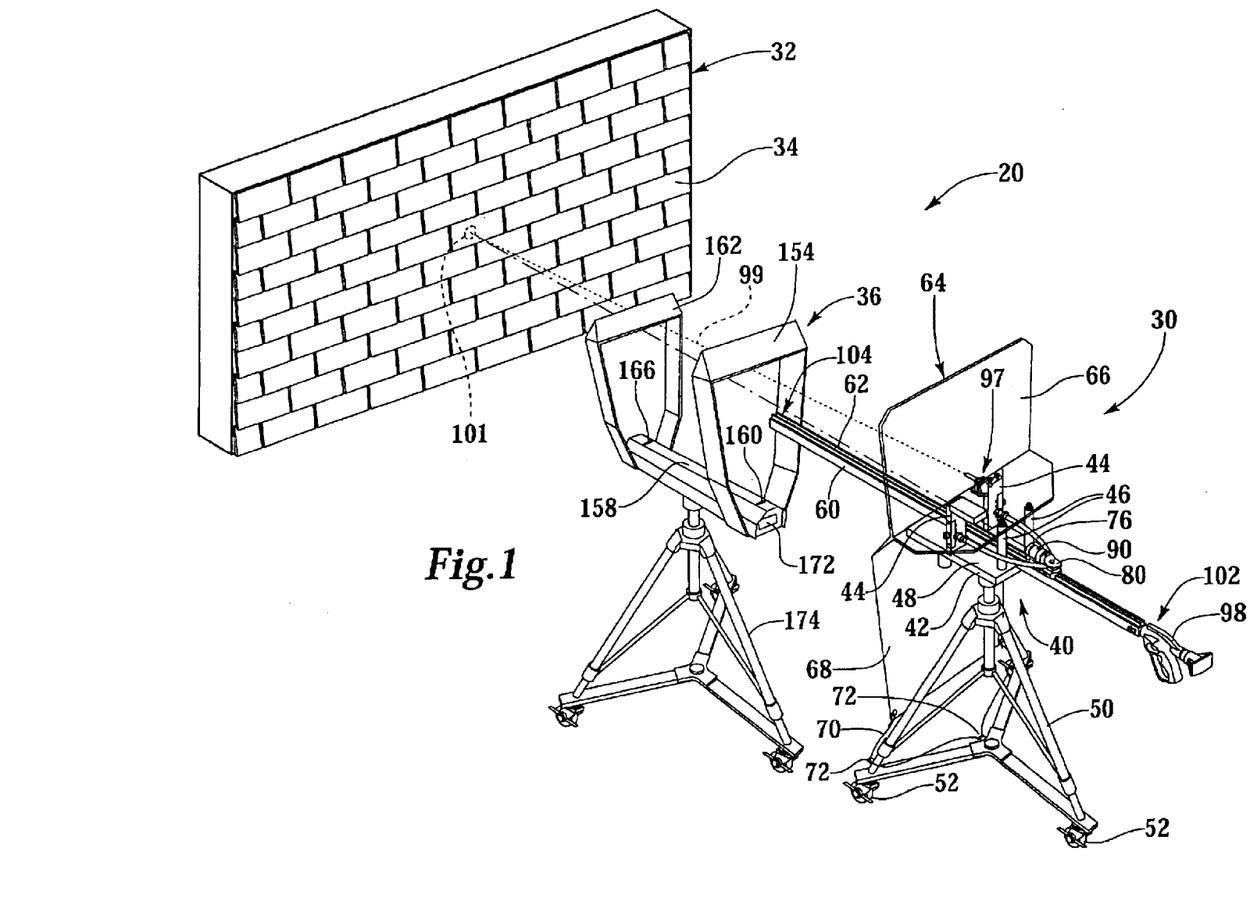
FIG. 1 shows the ice ball launcher of the present invention in a typical testing set-up configuration for simulating hailstone impact on roofing shingles.

FIG. 1 shows a typical testing configuration 20 for using the ice ball launcher of the present invention to simulate free-fall hailstone impact on specimen roofing shingles that have been attached to a roof structure mock-up. The testing configuration 20 includes an ice ball launcher 30, a roof structure mockup 32 having roofing shingles 34 installed thereon, and a velocity measuring device 36 located between the ice ball launcher 30 and the roof structure mockup 32. Preferably for testing a specific roofing material 34, a roof structure mockup 32 is fabricated to provide the same roof structure comparable to that found in a conventional building code installation of the roofing material 34.

For example, for testing roofing shingles designed for use on a residential home, the roof structure mockup 32 may include a wood beam frame covered with plywood decking and a layer of asphalt-saturated felt as a base for the roofing shingles. The roofing material 34 is preferably applied to the roof structure mockup 32 in accordance with the manufacturer's recommendations, building code standards, and/or industry standards. All types of roofing material may be tested in the testing configuration 20 shown in FIG. 1, including but not limited to: composite shingles, wood shingles and shakes, concrete tiles, slate tile, asphalt and stone coated metal paneling, for example. Therefore, for a given roofing material 34, the roof structure mockup 32 may vary accordingly.

Figure 3:
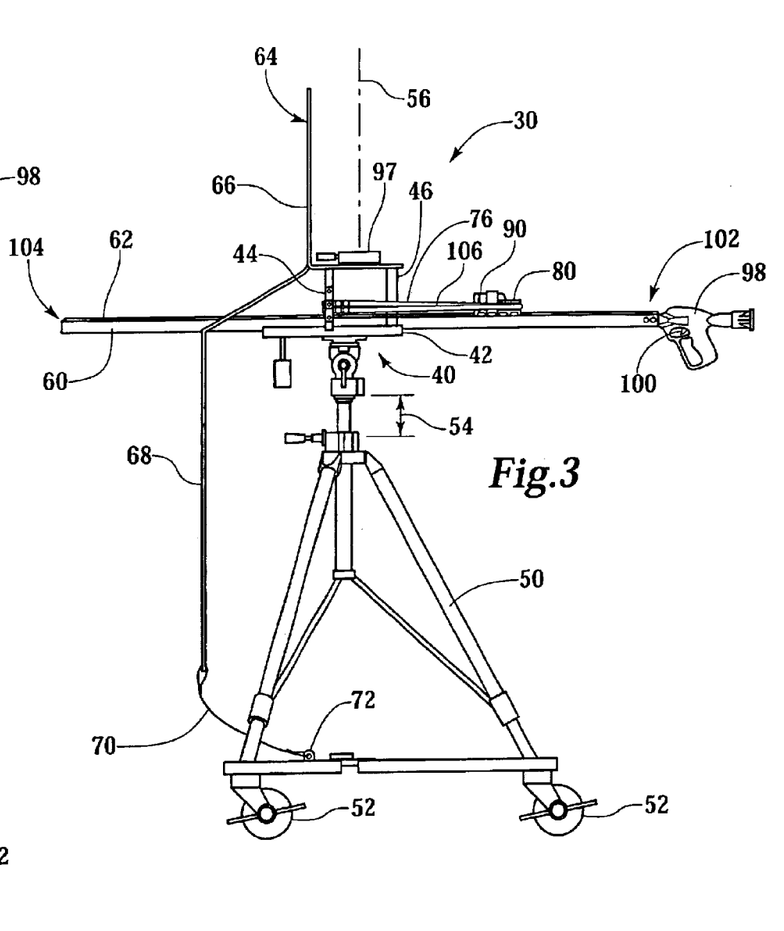
FIG. 3 is a side elevational view thereof.

The ice ball launcher 30 includes a base member 40 and a plate member 42 having two sets of column posts 44, 46 projecting generally perpendicular to a surface 48 of the plate member 42, and spaced apart on opposite sides of the rail. A tripod structure 50 with caster wheels 52 depending therefrom is removably attached to the plate member 42. Preferably, the caster wheels 52 of the tripod structure 50 are lockable to maintain the upright operable position of the ice ball launcher 30 at a predetermined distance from the test sample, as shown in FIG. 1 and FIG. 3. The tripod structure 50 shown FIG. 3 is adjustable in height as indicated by the dimension arrow 54, pivots about a vertical axis 56, and adjusts to different projection angles relative to the ground. The tripod structure 50 is a conventional tripod stand, for example of the type designed for photographic use. However, the base member 40 may include one of many different types of support members instead of or in addition to a tripod structure 50, including but not limited to: a table (not shown), a support frame (not shown), and/or a post (not shown).

A guide rail 60 is adjustably attached to the plate member 42. A channel portion 62 is attached on top of the guide rail 60. A shield 64 is attached to the base member 40. A top portion 66 of the shield 64 extends generally perpendicular to the rail 60 and the plate member 42. Preferably, the top shield portion 66 is a ⅜ inch thick sheet of transparent, shatterproof plastic. A bottom portion 68 of the shield 64 is made of plastic-coated material (but other materials, such as leather, may be used). The bottom shield portion 68 has a cable 70 connected to its bottom corners, and the cable 70 loops through clips 72 on the tripod structure 50. The shield 64 protects the user from reflected ice balls and/or shattered ice ball particles and target debris generated by impact.

Figure 5:
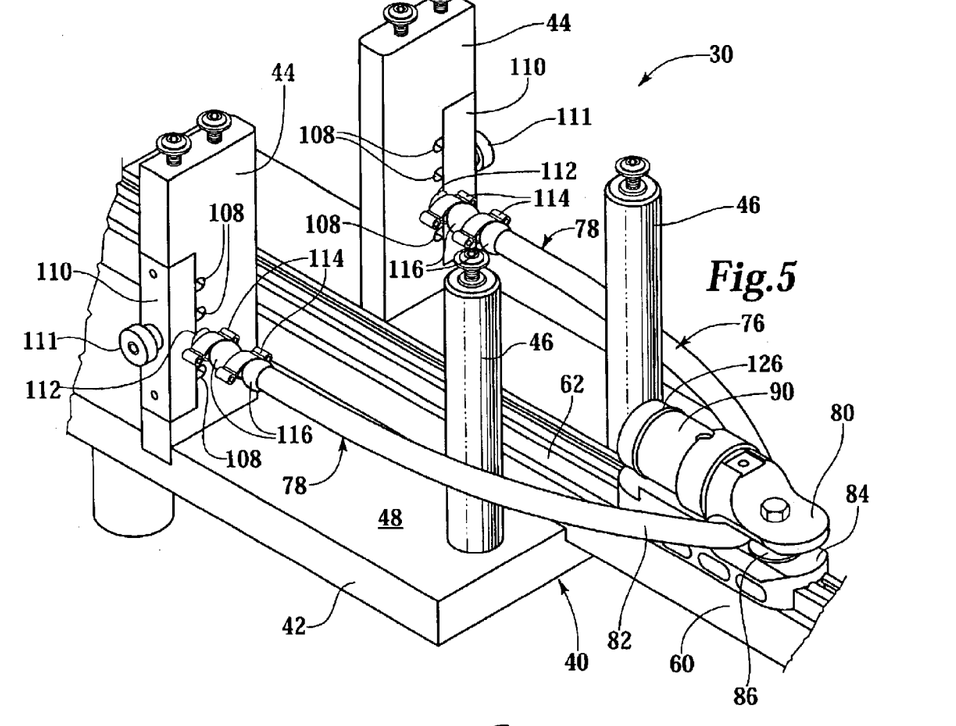
FIG. 5 is an enlarged perspective view of a portion of the ice ball launcher of FIG. 2.

As shown in FIG. 5, an elastic band 76 attaches to a pair of forward column posts 44 at its opposite end portions 78. The elastic band 76 extends to and engages with a sled 80. In the preferred embodiment, a central portion 82 of the elastic band 76 is threaded through a slot 84 in the sled 80, and a spool 86 is inserted into and bolted onto the sled. The spool slot 84 retains the central portion 82 of the elastic band 76 within the slot 84. As shown in FIG. 5, the pair of rear column posts 46 serve as stops to limit forward motion of the sled 80 when the elastic band 76 engages against the column posts 46.

Figure 6:
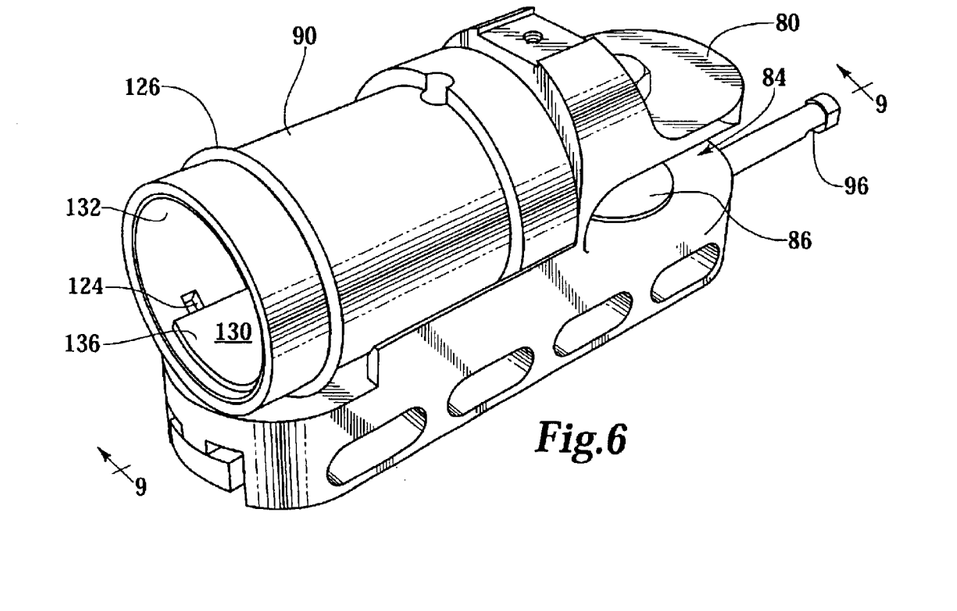
FIG. 6 is a front perspective view of a cup and sled combination.
Figure 7:
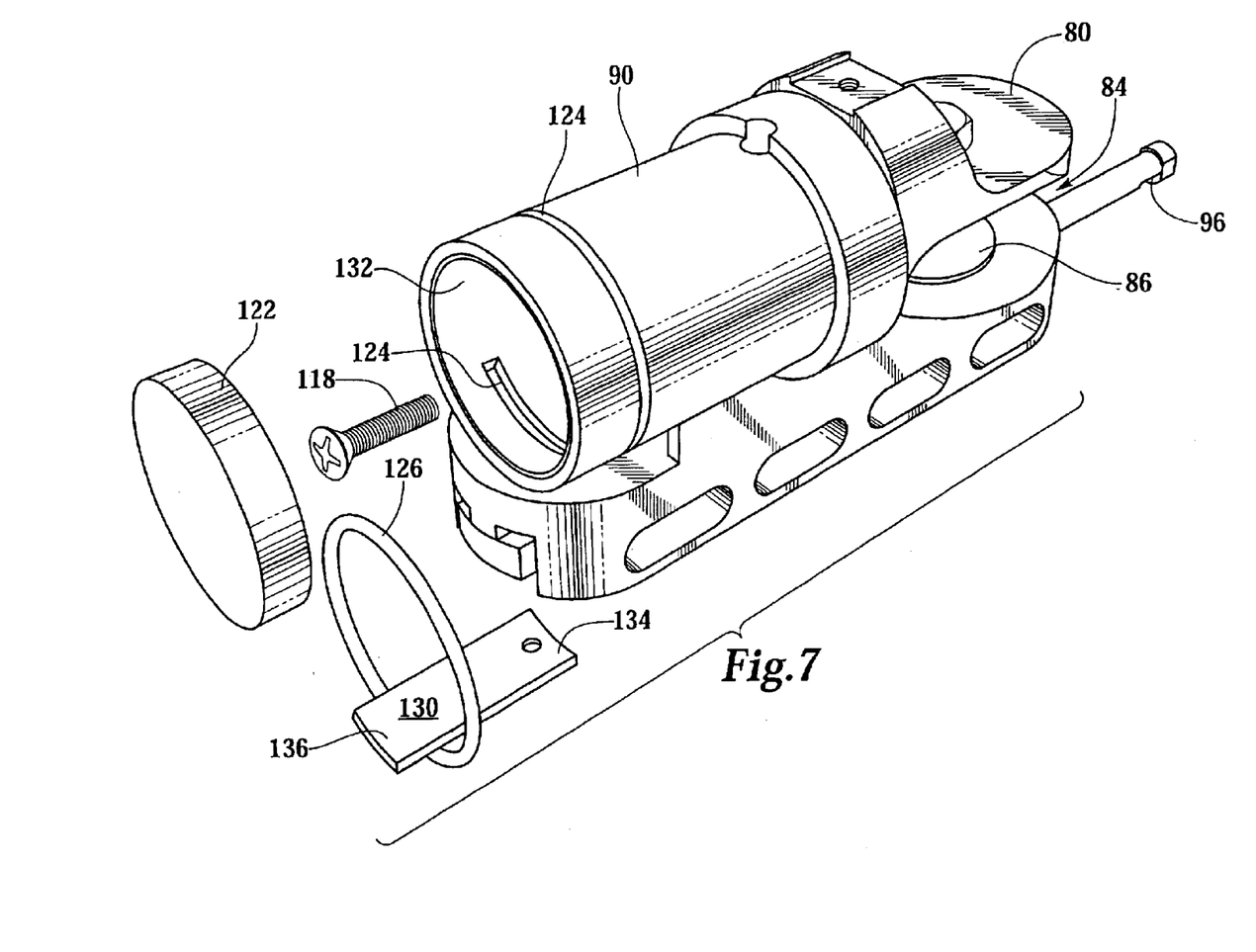
FIG. 7 is a partially exploded perspective view of the cup and sled combination of FIG. 6.
Figure 8:
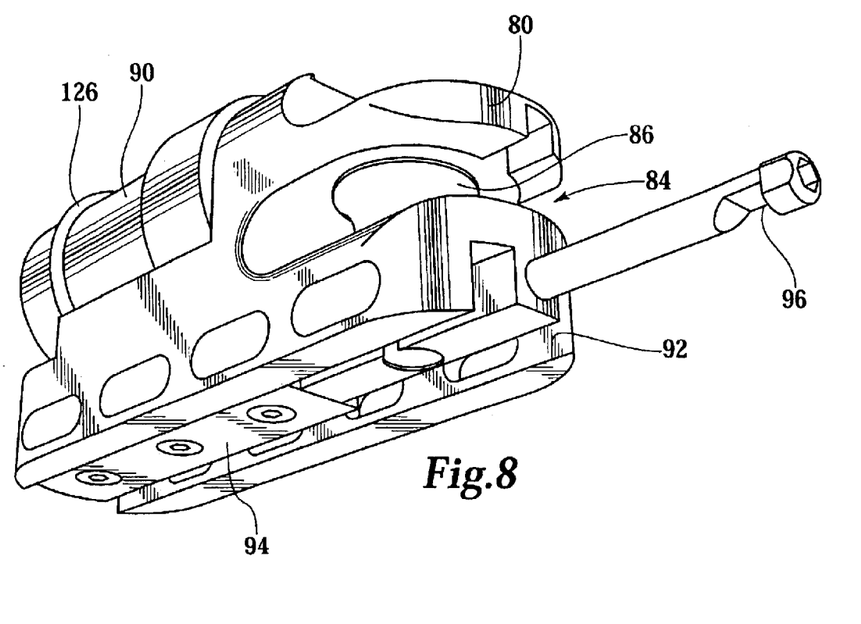
FIG. 8 is a bottom rear perspective view of the cup and sled combination of FIG. 6.
Figure 9:
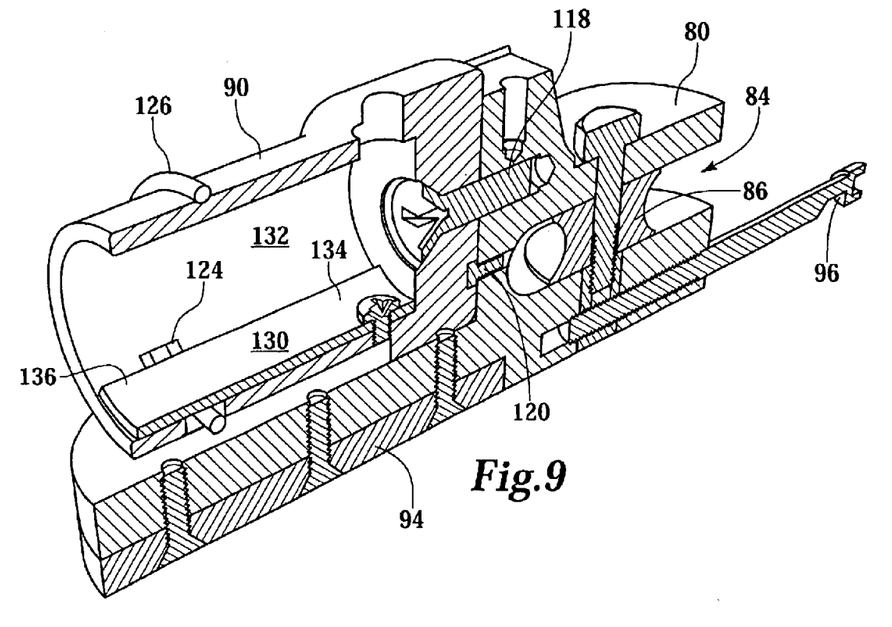
FIG. 9 is a cutaway view of the cup and sled combination of FIG. 6 taken along line 9—9.

FIGS. 6–9 show enlarged perspective views of the sled 80 in combination with an ice ball holder in the form of a receiver cup 90. As shown in FIGS. 8 and 9, the sled 80 has a slotted bottom 92, and a removable rail plate 94 that bolts to the slotted bottom 92 of the sled 80. The slotted sled bottom 92 and the sled rail plate 94 are shaped so that the sled 80 is slidably coupled with the channel portion 62 on the rail 60. The sled rail plate 94 retains the sled 80 in the channel 62 and on the rail 60, but it still allows the sled 80 to slide along the rail 60. As also shown in FIGS. 8 and 9, a trigger latch retainer 96 is threaded into and projects from the rear of the sled 80.

As shown in FIG. 3, an aiming device 97 is attached to the base member 40. The aiming device 97 of the preferred embodiment is adapted to emit a visible laser beam (e.g., red colored laser light). The laser aiming device 97 is a commercially available laser generator that emits a narrow beam of visible light, for example, of the kind used for target practice when attached to a pistol or rifle. The laser aiming device 97 of the first embodiment is battery powered, but may also be powered from an AC service wall outlet in other embodiments. The dashed line 99 shown in FIG. 1 represents a laser beam emitted from the laser aiming device 97. Hence, the laser aiming device 97 of the preferred embodiment projects a small red dot onto the roofing material 34 at the desired impact location 101. The impact location 101 is illustrated in a dashed line shown in FIG. 1. The ice ball launcher 30 may be calibrated so that the aim of the laser aiming device 97 is accurate to one millimeter or less for certain target distance ranges.

Referring again to FIGS. 1–3, a handle 98 with a trigger lever 100 is attached to an end 102 of the rail 60. The trigger lever 100 actuates a trigger latch within the handle 98. The trigger latch is adapted to releasably engage with the trigger latch retainer 96 when the ice ball launcher 30 is in a cocked configuration. Thus, in the cocked configuration, the sled 80 is pulled back to the end 102 of the rail 60 where the handle 98 and trigger lever 100 are located. In the cocked configuration, the first elastic band 76 is in a stretched, tensioned position pulling on the sled 80. When the trigger latch member is disengaged or released from the trigger latch retainer (after being cocked, i.e., when the launcher 30 is manually "fired"), the elastic band 76 pulls the sled 80 toward the forward end 104 of the rail 60. When the elastic band 76 engages the second pair of column posts 46, the forward motion of the sled 80 is suddenly stopped.

Figure 2:
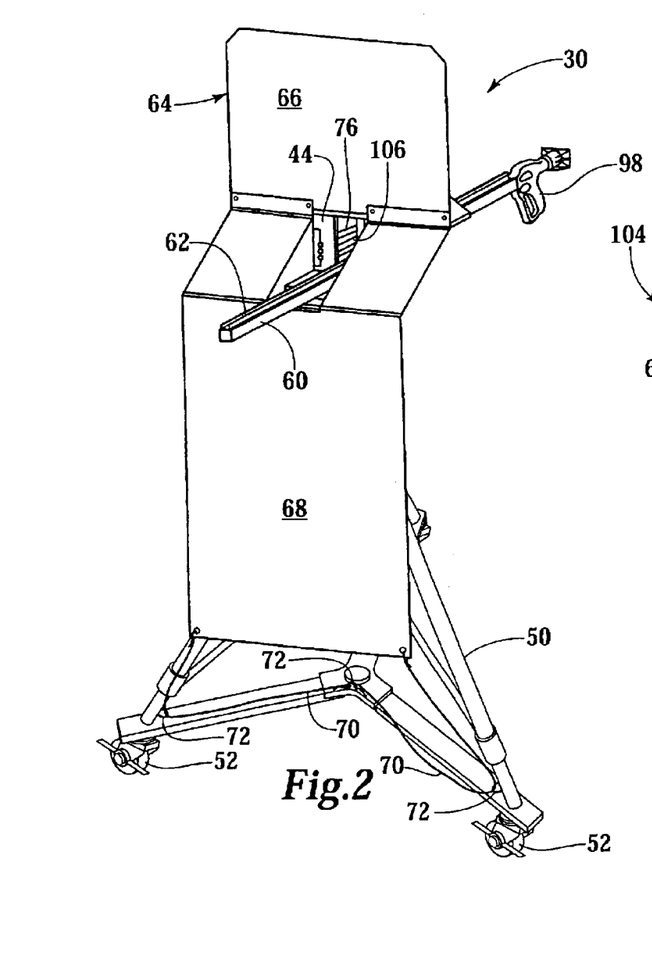
FIG. 2 is a front perspective view of the ice ball launcher of the present invention.
Figure 4:
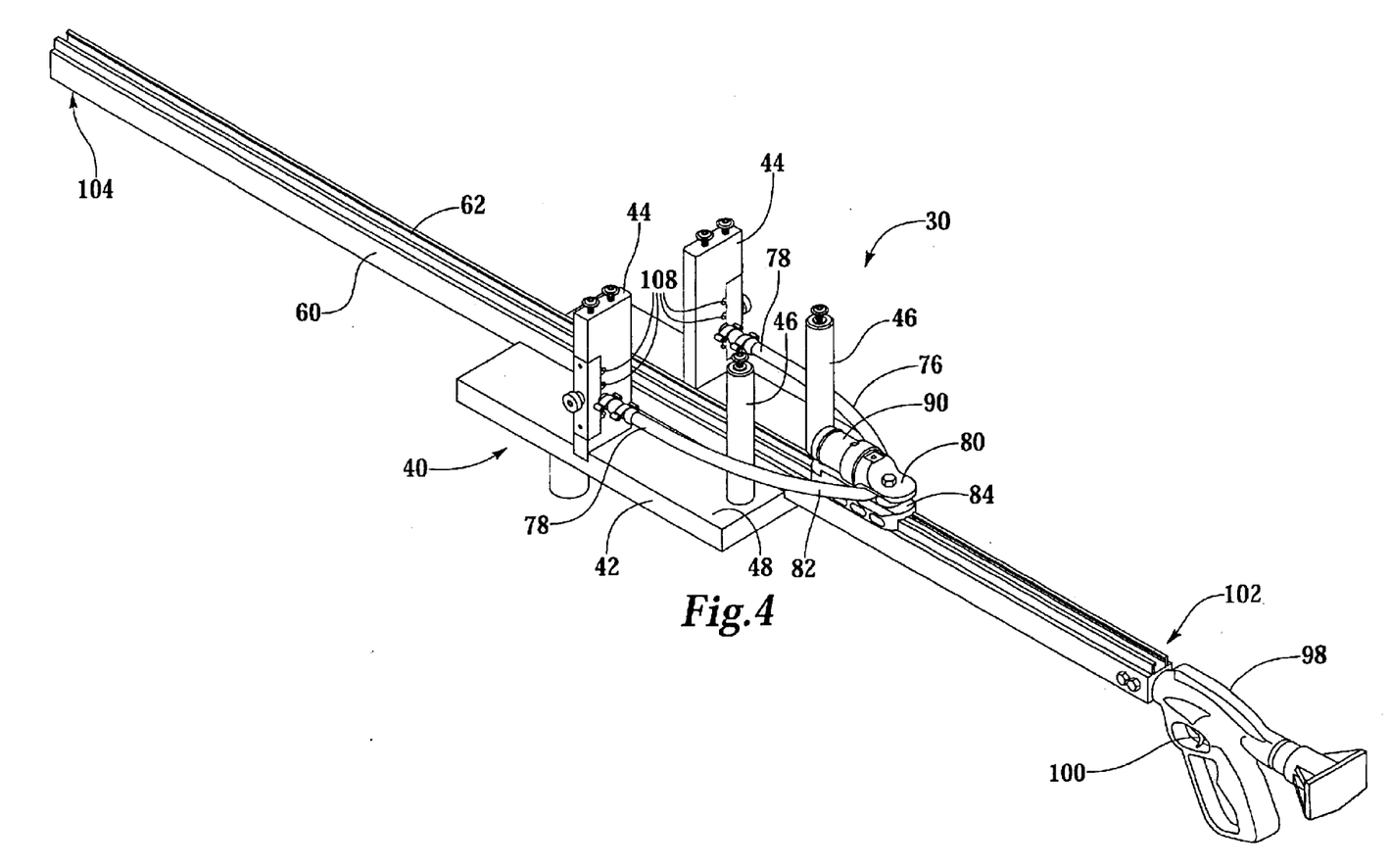
FIG. 4 shows a top perspective view of a portion of the ice ball launcher of FIG. 2.

In FIGS. 4 and 5, only one elastic band 76 is shown. However, as shown in FIGS. 2 and 3, two or more elastic bands 76, 106 may be used to increase the tension force exerted on the sled 80, and to thus increase the velocity and impact energy for a given ice ball size. As shown in FIG. 5, each column post 44 has four holes 108 for attaching up to four elastic bands. An elastic band retainer block 110 may be removed and reattached with a screw fastener 111 having a knurled knob for changing the number of elastic bands used. As also shown in FIG. 5, each end of the elastic band 76 is secured to an elastic band post 112 by two clamps 114. The elastic band posts 112 have ball-shaped projections 116 adjacent the location for the clamps 114 to better hold the elastic band 76 in place.

Referring to FIGS. 6–9, the cup member 90 is removably attached to the sled 80. The sled 80 is adapted to accept multiple cup sizes and shapes, as different cup sizes and shapes may be needed to releasably retain ice balls of different diameter sizes, for example ranging from about 3 cm to about 5 cm in nominal diameter. Preferably, there is a different cup size for each ice ball size. The cup member 90 shown in the first embodiment is held onto the sled 80 by a cup retainer screw 118 that threads into the sled 80.

A locating screw 120 has a head that extends from the sled 80 and mates with a corresponding hole or indention in the cup member 90 (see, e.g., FIGS. 7 and 9). The locating screw 120 helps in aligning the cup member 90 during installation onto the sled 80 and for keeping the cup member 90 from rotating after the cup member 90 is secured with the cup retainer screw 118. A foam plug 122 (shown in FIG. 7) is inserted into the cup member 90 to prevent an ice ball loaded in the receiver cup 90 from being pressed against a hard surface (e.g., the cup retainer screw 118) while the launcher 30 is being fired.

The receiver cup 90 has an interior surface configuration adapted to bias against and releasably retain an ice ball therein. The cup member 90 of the preferred embodiment has a groove 124 formed there through that extends partially about the cup member 90 in a circumferential direction. The outside surface of the receiver cup 90 may also have portions where the groove 124 is formed only partially through the receiver cup, which may be helpful in maintaining the position of an elastic o-ring retainer 126, as shown in FIG. 6. However, this portion of the groove 124 that does not extend through the cup member 90 is an optional feature.

In the preferred embodiment, a reed member 130 is attached to an interior surface 132 of the receiver cup 90 at one end 134 of the reed member 130 (see, e.g., FIG. 9), and the reed member 130 extends across at least a portion of the groove 124. The elastic o-ring retainer 126 is located about the receiver cup 90 within the groove 124. The elastic o-ring retainer 126 has an inner diameter smaller than an outer diameter of the receiver cup 90 where the groove 124 is located, which causes the elastic o-ring retainer 126 to extend into the receiver cup member and bias against the reed member 130.

When an ice ball of an appropriate size is placed within the receiver cup of FIG. 6, the free end 136 of the reed member 130 is lifted up and biased against the ice ball to temporarily retain the ice ball therein. Sometimes it may be desirable to aim the ice ball launcher 30 in a downward direction. Thus, the cup member 90 of the first embodiment will retain the ice ball therein while the launcher 30 is cocked and being aimed downward. However, when the sled 80 moves to the extent of its range of motion along the rail 60 when the launcher 30 is fired, the ice ball will be able to move past the reed member 130 and be expelled from the receiver cup. In other words, the momentum force of the ice ball will overcome the bias against the reed member 130 caused by the elastic o-ring retainer 126.

Figures 10, 11:
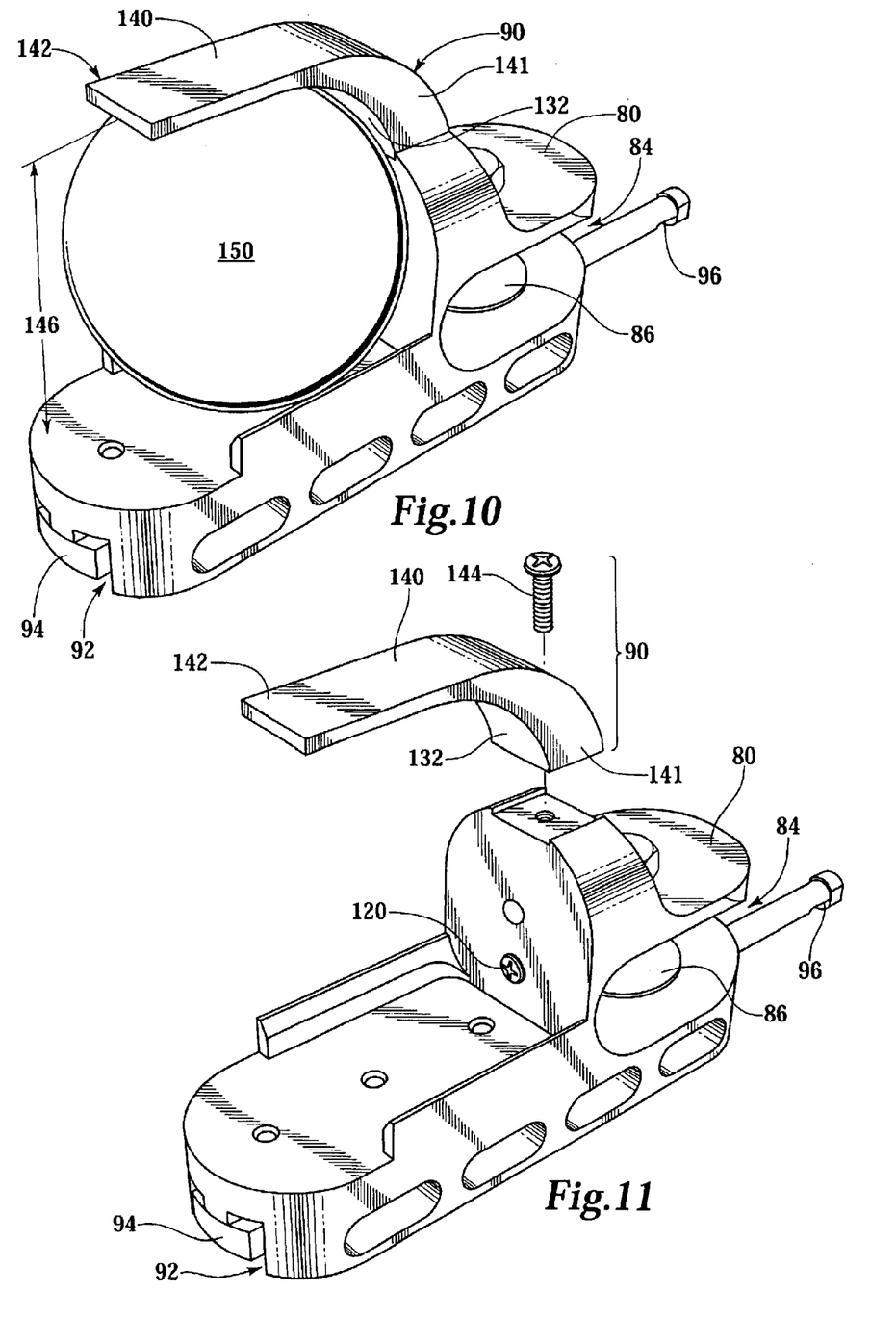
FIG. 10 is a front perspective view of a cup and sled combination according to an alternative embodiment with an ice ball loaded therein.
FIG. 11 shows a partially exploded perspective view of the cup and sled combination of FIG. 10.

FIGS. 10 and 11 show a combination of a sled 80 and ice ball holder 90 according to an alternative embodiment of the present invention. The sled 80 of the alternative embodiment is the same as previously described. The ice ball holder 90 of the alternative embodiment includes a clip member 140 with a proximate end 141 and a distal end 142. The proximate end 141 of the clip member 140 is removably attached to the sled 80 by a screw 144, and the distal end 142 extends over a portion of the sled 80. There is a first spaced distance 146 between the distal clip end 142 and the sled 80. The first spaced distance 146 is such that an ice ball 150 of a predetermined nominal diameter is releasably retained between the ice ball holder 90 and the sled 80 as the clip member 140 is biased against the ice ball 150 because the diameter of the ice ball 150 is slightly larger than that of the spacing distance 146.

The bias against the ice ball 150 in the second embodiment is caused by the flexure of the clip member 140 when the ice ball 150 is installed therein, which is dependent upon the difference between the first spaced distance 146 and the first diameter of the ice ball 150. Preferably, the bias force caused by the clip member 140 is strong enough to hold the ice ball 150 in place while the launcher 30 is cocked and aimed in a downward direction, but weak enough to allow the ice ball 150 to be readily inserted into the launcher 30 and to allow the ice ball 150 to be released when the sled 80 reaches the extent of its motion when the launcher 30 is fired. The alternative ice holder embodiment may be preferred for use with relatively larger ice balls, as compared to that of the first embodiment. The ice ball 150 shown in FIG. 10 has a nominal diameter of 5 cm, for example.

The ice balls preferred for use in the present invention are preferably made precisely so that the ice balls have a consistent diameter, temperature, shape and mass. The ice balls are preferably molded in a spherical mold (not shown) having a precise diameter. The ice balls are preferably maintained in a freezer chest at about −7±7 degrees F. (−22±4 degrees C.). The ice balls also preferably have a mass within ±0.226 grams (0.0005 lb.) within a given specification that may vary from about 15.3 grams for a 3 cm diameter ice ball to about 63 grams for a 5 cm diameter ice ball. The ice balls may be formed in a variety of different sizes for different tests, including but not limited to the following diameters: 1 inch (2.5 cm), 1¼ inches (3.18 cm), 1½ inches (3.81 cm), 1¾ inches (4.45 cm), 2 inches (5.08 cm) and 2¼ inches (5.7 cm), for example. Examples of the mass, simulated free-fall velocity, and impact energy during a test are stated in the following table:

| Nominal Ice Ball Diameter (inches) | Mass (pounds) | Free-fall Velocity (feet per second) | Kinetic Energy (Foot-Pound Force) |
|---|---|---|---|
| 1¼ | 0.0338 | 84.1 | 3.72 |
| 1½ | 0.0584 | 92.5 | 7.77 |
| 1¾ | 0.0928 | 101.8 | 14.95 |
| 2 | 0.1385 | 111.6 | 26.81 |

Preferably, the ice balls used for testing have no visible cracks. The ice balls should be launched and used for a test within 60 seconds of removal from the freezer chest to maintain consistency.

Figure 12:
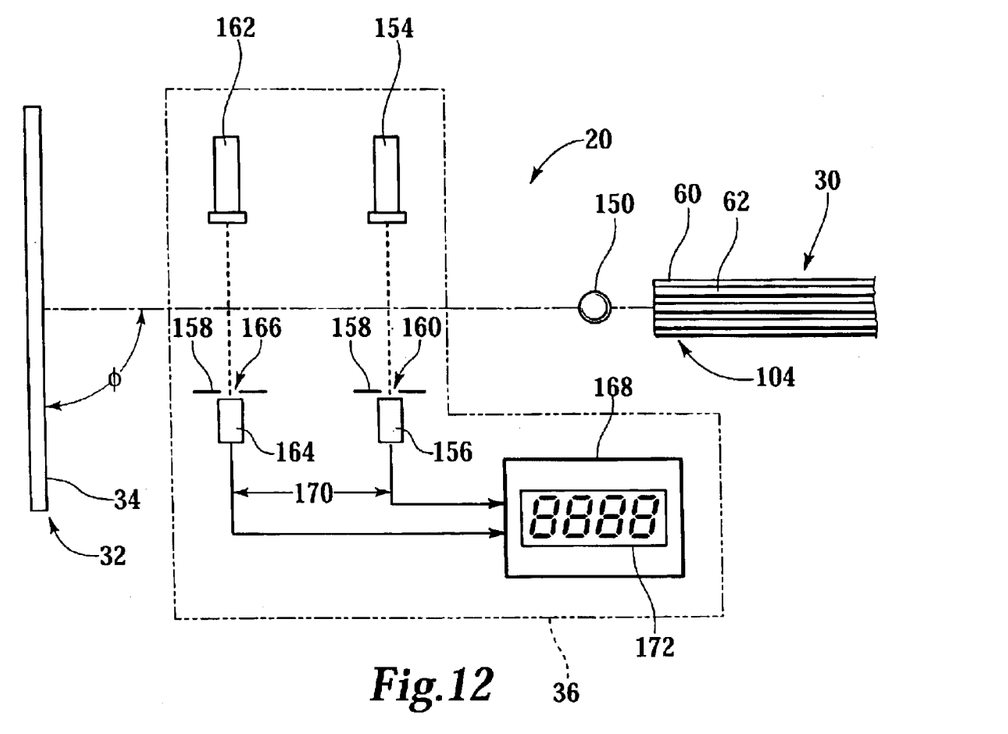
FIG. 12 is a schematic diagram illustrating the testing configuration of FIG. 1 in combination with a velocity measuring device.

Referring again to FIG. 1, during testing, the velocity of the ice ball is preferably measured with the velocity measuring apparatus 36 to verify that the test is being performed within established testing standards. The velocity measuring apparatus 36 shown in FIG. 1 is a commercially available velocity measuring device that includes a reflected light chronometer and an optoelectonic switch assembly. FIG. 12 is a schematic diagram illustrating the testing configuration 20 of FIG. 1 and illustrating operation of the velocity measuring device 36. The velocity measuring apparatus 36 of FIGS. 1 and 12 has a first light source 154 and a first light sensor 156. The first light sensor 156 is positioned below the first light source 154 and beneath a light shield member 158 that has a first slot 160 formed there through. Hence, the first light sensor 156 is positioned to receive light from the first light source 154 via the first slot 160.

The velocity measuring apparatus 36 of FIG. 1 also has a second light source 162 and a second light sensor 164, which may be the same type and size as those of the first light source 154 and first light sensor 156. A second slot 166 is formed through the light shield member 158 between the second light source 162 and the second light sensor 164. As shown in FIG. 12, the light sensors 156, 164 are electrically coupled by an electrical circuit 168. The electrical circuit 168 is adapted to detect a change in output from the first light sensor 156 when an object (e.g., an ice ball) passes between the first light source 154 and the first slot 160, and to detect a change in output from the second light sensor 164 when the object passes between the second light source 162 and the second slot 166.

The second light sensor 164 is located at a known and fixed distance 170 from the first sensor 156. The electrical circuit 168 then measures an elapsed time interval between the detected change in output from the first sensor 156 and the detected change in output from the second sensor 164. Based on this elapsed time measurement and based on the known fixed distance 170 between the first and second sensors 156, 164, the electrical circuit 168 then calculates the velocity of the object (the ice ball) passing through the velocity measurement device 36. The velocity measurement is then displayed on the digital display 172.

The velocity measurement device 36 shown in the embodiment of FIG. 1 is just one example of a commercially available velocity measuring device that may be used. In other embodiments of the present invention, other velocity measurement devices may be incorporated. For example, the velocity measurement device may be built into or onto the rail 60, rather than being a separate component on a separate tripod 174. With the benefit of this disclosure, one of ordinary skill in the art will likely realize many other variations for the velocity measuring device.

After measuring the velocity of an ice ball projected from the launcher 30, the kinetic energy of the ice ball at impact may be calculated to verify that it is within a given specification or standard for the test. The kinetic energy of the ice ball at impact may be calculated using the following equation:

$$KE=(mV_f^2)/64.34$$

where:

KE=ice ball kinetic energy, foot pound m=ice ball mass, pound $V_f$=ice ball free-fall speed, feet per second This value may be calculated manually using a calculator, for example, or it may be calculated automatically by the electrical circuit 168 and/or by a computer system (not shown) that is part of or coupled in communication with the launcher 30.

An embodiment of the present invention may be used to test, grade, and/or certify various structural components, for example roof shingles, skylights, vehicle windshields, automobile roof panels, aircraft fuselage panels, aircraft wing panels and the like. An example of such use in connection with roofing shingles will now be described. First, ice balls are precisely molded and made so that each ice ball is consistent within a tolerance range for temperature, diameter and mass, as described above. Next, a roof section mockup 32 having the roofing shingles 34 mounted thereon is set up. As described above, the roof section mockup 32 is preferably constructed in the same way as would be completed in an actual application.

Then, the ice ball launcher 30 is set up at the desired angle and distance from the roof section mock-up 32, as shown in FIG. 1. The launcher 30 may then be cocked. The laser aiming device 97 is aimed at the desired impact location 101 for the impact of the ice ball (see, e.g., FIG. 1). The velocity measuring device 36 is placed between the launcher 30 and the roof section mock-up 32 and within the path of the ice ball, as shown in FIG. 1, so that the ice ball will pass through the sensing zone of the velocity measuring device 36 after it is projected from the launcher 30. With the launcher 30 at the desired position, cocked, and aimed, it is ready to receive a fresh ice ball. Preferably before each ice ball is launched, it is weighed and inspected to verify its weight and to ensure that no cracks are visually seen.

Immediately after the ice ball is loaded into the cup 90 on the sled 80 of the launcher 30, the trigger lever 100 on the handle 98 is manually pressed by an operator to disengage the trigger latch members 96. After the ice ball is launched and impacts the roofing material 34, the velocity of the ice ball is displayed on the digital display 172 (see FIG. 12) and is noted to verify that it was within tolerance for the test. The impact energy may then be calculated and recorded also. The calculated impact energy may also be verified to determine whether it is within an impact tolerance range, which may be dictated by a standard or by testing criteria.

Next, the impact location 101 on the roofing shingles 34 may be inspected and evaluated to assess the damage to the roofing shingles 34 Based on the evaluation of the damage to the roofing shingles 34 by the ice ball impact, a relative integrity certification value, grade or quality factor may be assigned.

With the benefit of this disclosure, one of ordinary skill in the art will likely realize many different variations for forming other embodiments of the present invention. For example, the trigger lever 100 may be electrically actuated via a remote control (not shown) or via a computer controlled system (not shown). The sled 80 may be stopped on the rail 60 when the launcher is fired by an extension or bumper (not shown) on the rail 60 that engages the sled 80 rather engaging the first elastic member 76, for example. The entire system may be computer controlled and electrically actuated so that the aiming movement and firing may be performed remotely to keep the operator and observers out of harms way in another room or behind a protective wall, for example.

The preferred embodiment described herein is a portable system because it may be easily moved and/or used indoors an outdoors. An embodiment of the present invention may be entirely battery powered, or powered entirely from AC electrical wall outlet service, or it may be powered by a combination of batteries and wall outlet sources, for example.

The base member 40 and the rail member 60 may be formed from a single integral piece or may be formed from separate pieces, for example. Likewise, the channel portion 62 and the rail member 60 may be formed from a single integral piece (not shown) or may be formed from separate pieces, for example. Similarly, the base member 40, rail member 60, and the channel portion 62 may be formed from a single integral piece (not shown) or from separate pieces, for example. The first elastic member 76 may have one end attached to the base member 40 and/or the rail 60 (not shown), and may have its other end attached to the sled 80.

The aiming device may include a scope with cross hairs (not shown) for aiming, a two-part sight, a one part sight, and/or a laser emitter (see, e.g., FIG. 3), for example. The ice ball launcher 30 may further include a still camera (film or digital) and/or a video camera (film or digital) for producing documentary images of the ice ball impact. The materials used to make the components of the ice ball launcher 30 may include, but are not limited to: wood, metal, rubber, latex, vinyl, leather, plastic, composite, and/or any combination thereof, for example.

Although the invention has been described with reference to certain exemplary arrangements, it is to be understood that the forms of the invention shown and described are to be treated as preferred embodiments. In light of the description herein, various changes, substitutions, and modifications may be realized without departing from the spirit and scope of the invention as defined by the appended claims.

We claim:

1. Ice ball launch apparatus for simulating the impact of a hail stone falling on a structural component of an installation mockup test structure including one or more structural component samples disposed thereon for impact testing comprising, in combination:

a projectile launch platform including means for providing stable support for the launch platform at a predetermined projectile transit distance from an installation mockup test structure;

a rail attached to the launch platform;

a sled slidably coupled to the rail for movement to a cocked position and to a stop position on the rail;

an ice ball holder attached to the sled, the holder having a pocket for receiving an ice ball therein and including gripping means for temporarily retaining an ice ball in the pocket during set-up and aiming and for releasing the ice ball to allow it to cleanly separate from the holder;

a latch coupled to the sled, a trigger coupled to the rail and releasably engagable with the latch when the sled is in the cocked position;

a flexible elastic band coupled to the launch platform and engaging the sled, the elastic band being in a stretched condition pulling on the sled when the sled is in the cocked position; and apparatus for aiming the ice ball launcher toward an ice ball impact target.

2. The ice ball launch apparatus of claim 1, wherein the ice ball holder includes a cup member having a sidewall forming a pocket for receiving an ice ball, the cup sidewall being intersected by a groove that extends at least partially about the cup member in a circumferential direction, and further comprising:

a reed member disposed in the cup pocket and extending across at least a portion of the groove; and an elastic retainer member engaged about the cup member and disposed within the groove, the elastic retainer member having a relaxed diameter less than an outer diameter of the cup member where the groove is located such that the elastic band extends into the pocket and biases against the reed member.

3. The ice ball launch apparatus of claim 1, wherein the ice ball holder includes a clip member with a proximate end and a distal end, the proximate end of the clip member being removably attached to the sled, the distal end extending over a portion of the sled, the distal end of the clip member being separated from the sled by a spacing distance such that the clip member and the sled are adapted to releasably retain an ice ball having a nominal diameter there between, wherein the nominal diameter is larger than the spacing distance.

4. The ice ball launch apparatus of claim 1, wherein the sled is adapted to accept multiple ice ball holder sizes and shapes for releasably retaining multiple ice ball sizes.

5. The ice ball launch apparatus of claim 1, further comprising one or more additional elastic bands coupled to the base member and engaging the sled.

6. The ice ball launch apparatus of claim 1, wherein the launch platform includes a tripod structure with wheels extending therefrom.

7. The ice ball launch apparatus of claim 1, wherein the launch platform includes a plate member having a plurality of column posts projecting generally perpendicular to a surface of the plate member, wherein the opposite end portions of the elastic band are attached to a pair of the column posts.

8. The ice ball launch apparatus of claim 7, wherein the plurality of column posts include a second pair of column posts longitudinally spaced from the first pair of column posts, the second pair of column posts serving as stops for engaging the elastic band in order to arrest forward motion of the sled at the stop position on the rail.

9. The ice ball launch apparatus of claim 1, wherein the elastic band includes first and second end portions attached to the base member and an intermediate portion engaging the sled.

10. The ice ball launch apparatus of claim 1, wherein the aiming device comprises laser apparatus for emitting a visible laser beam.

11. The ice ball launch apparatus of claim 1, further comprising a shield attached to the launch platform and extending generally perpendicular to the rail.

12. The ice ball launch apparatus of claim 1, further comprising velocity measuring apparatus for measuring the velocity of an ice ball projected from the ice ball launcher.

13. The ice ball launch apparatus of claim 12, wherein the velocity measuring apparatus includes:
  a first light source;
  a first light sensor positioned to receive light from the first light source;
  a second light source;
  a second light sensor positioned to receive light from the second light source, wherein the second light sensor is located at a fixed distance away from the first light sensor; and
  an electrical circuit adapted to:
  detect a change in output from the first light sensor;
  detect a change in output from the second light sensor;
  measure a time interval elapsed between the detected change in output from the first light sensor and the detected change in output from the second light sensor; and
  calculate the velocity of the ice ball first passing between the first light source and the first light sensor and then passing between the second light source and the second light sensor.

14. An ice ball launcher, comprising:
  a base member, the base member including a support stand;
  a rail attached to the base member, the rail including a channel portion thereon;
  a sled slidably coupled with the channel portion for movement to a cocked position on the rail and for movement to a stop position on the rail;
  a trigger latch retainer extending from the sled;
  a trigger latch member coupled to the rail, the trigger latch member being adapted to releasably engage with the trigger latch retainer;
  an elastic band including opposite end portions coupled to the base member and a central portion engaging the sled, the elastic band being in a stretched condition under tension and pulling on the sled when the sled is in the cocked position;
  a cup member removably attached to the sled, the cup member including an interior configuration adapted to bias against and releasably retain an ice ball therein, wherein the cup member has a groove formed there through that extends partially about the cup member in a circumferential direction;
  a reed member attached to an interior surface of the cup member at one end of the reed member, the reed member extending across at least a portion of the groove;
  aiming apparatus attached to the base member, the aiming apparatus being adapted to emit a visible laser beam;
  column posts projecting generally perpendicular form the base member, the end portions of the elastic band being attached to a first pair of the column posts, respectively, and the central portion of the elastic band engages the sled, and including a second pair of the column posts disposed forward of the first pair thereby serving as travel stops for engaging the central portion of the elastic band to limit a range of motion for the sled;
  a shield attached to the base member and extending generally perpendicular to the rail; and
  velocity measuring apparatus for measuring the velocity of an ice ball projected from the ice ball launcher, wherein the velocity measuring device includes:
  a first light source,
  a first light sensor positioned to receive light from the first light source,
  a second light source,
  a second light sensor positioned to receive light from the second light source, wherein the second light sensor is located at a fixed distance away from the first light sensor, and
  an electrical circuit for:
  detecting a change in output from the first light sensor,
  detecting a change in output from the second light sensor,
  measuring a time interval elapsed between the detected change in output from the first light sensor and the detected change in output from the second light sensor, and
  calculating the velocity of an ice ball first passing between the first light source and the first light sensor and then passing between the second light source and the second light sensor.

15. Apparatus for simulating the impact of a hail stone falling onto a structural component sample in an installation mockup test structure including one or more structural component samples mounted thereon for testing comprising, in combination:
  an ice projectile having a predetermined mass and diameter that simulates naturally occurring hail;
  a projectile launch including a launch platform and means for providing stable support for the platform at a predetermined projectile transit distance from an installation mockup test structure, the launch including a rail mounted on the platform, a sled mounted for sliding movement along the rail and an ice ball holder carried on the sled for releasably holding an ice ball;
  one or more elastic bands attached to the platform and coupled to the sled for accelerating the sled along the rail upon release of stretching tension;
  a manually operable latch and trigger assembly coupled to the rail and engagable with the sled for holding the elastic band under tension while the sled is held at a cocked position and for releasing the sled by manual actuation of the trigger;

stop means engagable with the sled or the elastic band for arresting motion of the sled as it accelerates near the forward end of the rail; and gripping means mounted on or in the ice ball holder for temporarily retaining an ice projectile in the receiver cup during set-up and aiming and for releasing the ice projectile to allow it to cleanly separate from the holder in response to sudden deceleration of the sled as forward motion of the sled is arrested by the stop means.

16. Apparatus for simulating the impact of a hail stone falling onto a structural component sample in an installation mockup test structure as set forth in claim 15, wherein the gripping means comprises an elastic O-ring.

17. Apparatus for simulating the impact of a hail stone falling onto a structural component sample in an installation mockup test structure as set forth in claim 15, wherein the gripping means comprises a resilient clip.

18. Apparatus for simulating the impact of a hail stone falling onto a structural component sample in an installation mockup test structure as set forth in claim 15, further comprising:

aiming apparatus mounted on the launch platform for accurately aiming the rail and the projectile flight path so that the ice projectile will impact at a desired impact point on the test structure.

19. Apparatus for simulating the impact of a hail stone falling onto a structural component sample in an installation mockup test structure as set forth in claim 18, wherein the aiming apparatus comprises a laser beam projector.

20. Apparatus for simulating the impact of a hail stone falling onto a structural component sample in an installation mockup test structure as set forth in claim 15, further comprising:

velocity measuring apparatus for computing the velocity of the ice projectile as it transits the flight path between the launch and the test structure.

21. Apparatus for simulating the impact of a hail stone falling onto a structural component sample in an installation mockup test structure as set forth in claim 20, wherein the velocity measuring apparatus comprises a reflected light chronometer and an optoelectonic switch assembly.

22. A method of simulating hail stone impact on a structural component sample, comprising the steps:

molding an ice ball of a predetermined size;

providing an installation mockup having a structural component sample installed thereon;

positioning an ice ball launcher at a predetermined distance from the installation mockup;

aiming the ice ball launcher at a specific location aiming point on the component sample;

loading the ice ball into the ice ball launcher, and projecting the ice ball from the ice ball launcher at a predetermined velocity onto the specific location aiming point on the component sample.

23. The method of claim 22, further comprising:

measuring the velocity of the ice ball as it transits between the ice ball launcher to the component sample; and determining whether the ice ball velocity is within a predetermined velocity tolerance range.

24. The method of claim 23, further comprising:

calculating an impact energy of the ice ball impacting the component sample; and determining whether the calculated impact energy is within a predetermined impact energy tolerance range.

25. The method of claim 22, further comprising:

measuring the indentation depth on the component sample caused by the ice ball impact; and assigning a relative integrity certification value to the component sample based on the indentation measurement.

26. Apparatus for simulating the impact of a hail stone falling onto a structural component sample in an installation mockup test structure including one or more structural component samples mounted thereon for testing comprising, in combination:

a launch platform for providing stable support for an ice ball launcher at a predetermined projectile transit distance from an installation mockup test structure an ice ball launcher mounted on the launch platform;

apparatus for aiming the ice ball launcher toward an ice ball impact target on a component sample; and velocity measuring apparatus for measuring the velocity of an ice ball projected from the ice ball launcher toward the impact target.

27. Apparatus for simulating the impact of a hail stone falling onto a structural component sample in an installation mockup test structure as set forth in claim 26, wherein the aiming apparatus comprises a laser beam projector for projecting a visible laser beam on a structural component sample.

28. Apparatus for simulating the impact of a hail stone falling onto a structural component sample in an installation mockup test structure as set forth in claim 26, wherein the velocity measuring apparatus comprises a reflected light chronometer and an optoelectonic switch assembly.

29. Apparatus for simulating the impact of a hail stone falling onto a structural component sample in an installation mockup test structure as set forth in claim 26, including a transparent shield attached to the launch platform for protecting an operator during launching operations.

30. Apparatus for simulating the impact of a hail stone falling onto a structural component sample in an installation mockup test structure as set forth in claim 26, the launch platform comprising a portable tripod assembly.

* * * * *